(12) United States Patent
Chang et al.

(10) Patent No.: US 12,274,987 B2
(45) Date of Patent: Apr. 15, 2025

(54) PLATELET FILTRATION MEMBRANE AND ITS APPLICATIONS THEREOF

(71) Applicant: CHUNG YUAN CHRISTIAN UNIVERSITY, Tao-Yuan (TW)

(72) Inventors: Yung Chang, Tao-Yuan (TW); Chih Chen Yeh, Tao-Yuan (TW)

(73) Assignee: CHUNG YUAN CHRISTIAN UNIVERSITY, Tao-Yuan (TW)

( * ) Notice: Subject to any disclaimer, the term of this patent is extended or adjusted under 35 U.S.C. 154(b) by 624 days.

(21) Appl. No.: 17/520,742

(22) Filed: Nov. 8, 2021

(65) Prior Publication Data

US 2023/0148415 A1    May 11, 2023

(51) Int. Cl.
| | |
|---|---|
| *A61K 35/19* | (2015.01) |
| *A61K 35/16* | (2015.01) |
| *B01D 69/02* | (2006.01) |
| *B01D 69/10* | (2006.01) |
| *B01D 71/80* | (2006.01) |
| *G01N 1/40* | (2006.01) |

(52) U.S. Cl.
CPC .............. *B01D 69/10* (2013.01); *A61K 35/16* (2013.01); *A61K 35/19* (2013.01); *B01D 69/02* (2013.01); *B01D 71/80* (2013.01); *G01N 1/4005* (2013.01); *B01D 2325/02* (2013.01); *B01D 2325/04* (2013.01); *G01N 2001/4016* (2013.01)

(58) Field of Classification Search
None
See application file for complete search history.

*Primary Examiner* — Russell G Fiebig
(74) *Attorney, Agent, or Firm* — WPAT, PC (57) ABSTRACT

A platelet filtration membrane and its application for preparing platelets rich plasma and separating platelets from blood samples are disclosed. The platelet filtration membrane comprises a coating layer and a porous substrate. The coating layer composition comprises a first copolymer having a plurality of amide groups and a second copolymer having a plurality of carboxylic acid groups, and the porous substrate comprises PE, PP, PS, PET, PTFE, PVDF, ceramic or rayon. The coating layer is on surfaces of the porous substrate to form the platelet filtration membrane.

19 Claims, 9 Drawing Sheets

PLATELET FILTRATION MEMBRANE AND ITS APPLICATIONS THEREOF

TECHNICAL FIELD

The invention relates to a novel platelet filtration membrane and its application on preparation of platelets rich plasma as well as platelets separation. In particular, the platelet filtration membrane comprises a thermal-responsive layer that coated on surfaces of a porous substrate.

BACKGROUND

In biomedical area, platelets separation from blood samples is mainly performed by a platelets centrifugation process. However, the platelets centrifugation process has a lot of drawbacks. For instance, the platelets centrifugation process is expensive, difficult to control and easy to cause cross-pollutions of final platelets separation product. Moreover, the platelets plasma obtained by the platelets centrifugation process has more leukocyte residue and is overactive, so it is not able to use in treatment of sickness, such as arthritis or wound-healing. As a result, the platelets plasma obtained by current platelet centrifugation processes does not satisfy quality requirements of bio-medicines, so limit their applications on curing many diseases.

Based on the above, there is still an urgent need for developing a novel platelets separation technology in biomedical fields.

SUMMARY OF THE INVENTION

According to the aforementioned background, the invention is directed to a novel platelet filtration membrane and its application on preparation of platelets rich plasma as well as platelets separation.

In one aspect, the invention discloses a platelet filtration membrane. Particularly, the platelet filtration membrane comprises a layer that coated on surfaces of a porous substrate. The porous substrate has a micron-size pore structure for providing effective channels for filtering a blood sample. Moreover, the layer is thermal-responsive and has a nanometer thickness, so as to capture platelets from the blood sample onto it and release the platelets from the layer at different temperature, respectively. Preferably, the layer captures platelets from the blood sample onto it at about 30-40° C. and releases the platelets from the layer at about 0-20° C.

Specifically, a composition of the layer comprises at least two types of copolymer. One is a thermal responsive type copolymer and another is a protein-conjugated type copolymer. Firstly, the thermal responsive type copolymer is a copolymer having a plurality of amide groups. The copolymer having a plurality of the amide groups comprises poly(N-isopropyl acrylamide)-poly(butyl methacrylate), poly(N-isopropyl acrylamide)-poly(styrene) or their analogues. Secondly, the protein-conjugated type copolymer is a copolymer having a plurality of carboxylic acid groups. The copolymer having a plurality of the carboxylic acid groups comprises poly(acrylic acid)-poly(butyl methacrylate) or its analogues.

A mixture or composition comprises the thermal responsive type copolymer and protein-conjugated type copolymer is able to capture platelets from the blood sample onto it and release the platelets from the layer at different temperature, respectively.

Additionally, both of the aforementioned copolymers comprise block copolymers, random copolymers or alternative copolymers.

In one representative embodiment, the platelet filtration membrane comprises the layer that coated on surfaces of the porous substrate. The composition of the layer comprises poly(N-isopropyl acrylamide)-b-poly(butyl methacrylate)-b-poly(N-isopropyl acrylamide) and poly(acrylic acid)-b-poly(butyl methacrylate)-b-poly(acrylic acid), and the porous substrate comprises poly(ethylene), poly(propylene), poly(styrene), polyethylene terephthalate, polytetrafluoroethylene, polyvinylidene fluoride, ceramic or rayon.

In one representative embodiment, the platelet filtration membrane is a thermal-responsive membrane, so as to capture platelets from the blood sample onto surfaces of the platelet filtration membrane and release the platelets from surfaces of the platelet filtration membrane at different temperature, respectively. Preferably, the platelet filtration membrane captures platelets from the blood sample onto it at about 30-40° C. and releases the platelets from it at about 0-20° C.

In another representative embodiment, the platelet filtration membrane comprises a layer that has a first water contact angle between 50 and 60 degree at about 37° C., and a second water contact angle between 20 and 40 degree at about 20° C.

In another aspect, the invention provides a method for preparing platelet rich plasma (PRP). Specifically, the method for preparing platelet rich plasma is able to prevent the platelets from activation and damage during the preparation of PRP. As a result, good qualities of the platelet rich plasma are obtained by the invented method.

Representatively, the method comprises following steps.

Step 1: contacting a blood sample with the platelet filtration membrane as defined in the aforementioned at about 30-40° C. for 10 minutes at least for adsorbing platelets onto the platelet filtration membrane.

Step 2: removing non-adsorbing content of the blood sample from the platelet filtration membrane at about 30-40° C. by a filtering process and the filtering rate is about 10 ml/min.

Step 3: washing the platelet filtration membrane obtained at step (2) by a first liquid at about 30-40° C.

Step 4: cooling the platelet filtration membrane obtained at step (3) to 0~10° C. for releasing the platelets from the platelet filtration membrane.

Step 5: washing the platelets released at step (4) by a second liquid at about 0~10° C. to a receiver for obtaining the platelet rich plasma.

Particularly, the method for preparing platelet rich plasma has 75-90% of platelet recovery, 2-5% of red blood cell residual percent and less than 0.0025% of white blood cell residual percent.

The method is to use the platelet filtration membrane to capture platelets from blood sample onto it and release the platelets from it at different temperature, respectively, because the platelet filtration membrane comprises the layer comprises the thermal-responsive type copolymers and protein-conjugated type copolymers. Preferably, the layer captures platelets from the blood sample at about 30-40° C. and releases the platelets from the layer at about 0-20° C.

In still another aspect, the invention provides a method for separating platelets from a blood sample. The method comprises following steps.

Step 1: contacting a blood sample with the platelet filtration membrane as defined in the aforementioned aspect at about 30~40° C. for 10 minutes at least for adsorbing platelets onto the platelet filtration membrane.

Step 2: removing non-adsorbing content of the blood sample from the platelet filtration membrane at about 30~40° C. by a filtering process and the filtering rate is about 10 ml/min.

Step 3: washing the platelet filtration membrane obtained at step (2) by a liquid at about 30~40° C.

Step 4: cooling the platelet filtration membrane obtained at step (3) to 0~10° C. for releasing the platelets from the platelet filtration membrane, so as to separate the platelets from the blood sample.

Particularly, the method for separating platelets from the blood sample has 75-90% of platelet recovery, 2-5% of red blood cell residual percent and less than 0.0025% of white blood cell residual percent.

In brief, the invented platelet filtration membrane comprises a layer that coated on surfaces of a porous substrate. The porous substrate has a micron-size pore structure for providing effective channels for filtering a blood sample. Moreover, the layer has a nanometer thickness and comprises at least two types of copolymer. One is a thermal responsive type copolymer and another one is a protein-conjugated type copolymer, so as to capture platelets from the blood sample onto it and release the platelets from the layer at different temperature, respectively. Preferably, the layer captures platelets from the blood sample onto it at about 30-40° C. and releases the platelets from the layer at about 0-20° C. Furthermore, the aforementioned methods for preparing platelet rich plasma and platelets separation by using the platelet filtration membrane are able to prevent the platelets from activation and damage during the process. As a result, PDGF and TGF are reserved in the platelet rich plasma content and good qualities of the platelets rich plasma are obtained. Typically, the aforementioned methods for preparing platelet rich plasma and platelets separation by using the platelet filtration membrane have 75-90% of platelet recovery percent, 2-5% of red blood cell residual percent and less than 0.0025% of white blood cell residual percent.

EMBODIMENTS

In a first embodiment, the invention discloses a platelet filtration membrane. Particularly, the platelet filtration membrane comprises a layer that coated on surfaces of a porous substrate. The porous substrate has a micron-size pore structure for providing effective channels for filtering a blood sample. Moreover, the layer has a nanometer thickness and is good to capture platelets from the blood sample onto the layer and release the platelets from the layer at different temperature, respectively. Preferably, the layer captures/binds platelets from the blood sample onto it at about 30-40° C. and releases/desorbs the platelets from the layer at about 0-20° C., respectively.

Specifically, the layer composition comprises at least two types of copolymer. One is a thermal responsive type copolymer and another one is a protein-conjugated type copolymer. Typically, the thermal responsive type copolymer is a copolymer having a plurality of amide groups. The copolymer having a plurality of the amide groups comprises poly(N-isopropyl acrylamide)-poly(butyl methacrylate), poly(N-isopropyl acrylamide)-poly(styrene) or their analogues. The protein-conjugated type copolymer is a copolymer having a plurality of carboxylic acid groups. The copolymer having a plurality of the carboxylic acid groups comprises poly(acrylic acid)-poly(butyl methacrylate) or its analogues.

In one example of the first embodiment, a mixture or composition comprises the thermal responsive type copolymer and protein-conjugated type copolymer is able to capture/bind platelets from the blood sample onto it and release/desorb the platelets from it at different temperature, respectively.

In another example of the first embodiment, both of the aforementioned copolymers comprise block copolymers, random copolymers or alternative copolymers.

In one example of the first embodiment, the platelet filtration membrane comprises a layer that coated on surfaces of a porous substrate, and the layer composition comprises at least a first copolymer having a plurality of amide groups and a second copolymer having a plurality of carboxylic acid groups, and the porous substrate comprises poly(ethylene), poly(propylene), poly(styrene), polyethylene terephthalate, polytetrafluoroethylene, polyvinylidene fluoride, ceramic or rayon.

In one example of the first embodiment, the first copolymer having a plurality of the amide groups comprises poly(N-isopropyl acrylamide)-poly(butyl methacrylate), or poly(N-isopropyl acrylamide)-poly(styrene).

In another example of the first embodiment, the second copolymer having a plurality of the carboxylic acid groups comprises poly(acrylic acid)-poly(butyl methacrylate).

In one representative example of the first embodiment, the platelet filtration membrane comprises a layer that coated on surfaces of a porous substrate, and the layer composition comprises poly(N-isopropyl acrylamide)-b-poly(butyl methacrylate)-b-poly(N-isopropyl acrylamide) and poly(acrylic acid)-b-poly(butyl methacrylate)-b-poly(acrylic acid). The porous substrate comprises the porous substrate comprises poly(ethylene), poly(propylene), poly(styrene), polyethylene terephthalate, polytetrafluoroethylene, polyvinylidene fluoride, ceramic or rayon.

In one example of the first embodiment, the layer has a thickness between 20 and 50 nm.

In one example of the first embodiment, the layer has a first water contact angle between 50 and 60 degree at about 37° C., and a second water contact angle between 20 and 40 degree at about 20° C.

In one example of the first embodiment, weight percent of the first copolymer having a plurality of the amide groups is about 60-80% and weight percent of the second copolymer having a plurality of the carboxylic acid groups is about 20-40%, and the weight percent is calculated based on total weight of the layer.

In one representative example of the first embodiment, weight percent of the poly(N-isopropyl acrylamide)-b-poly (butyl methacrylate)-b-poly(N-isopropyl acrylamide) is about 60-80% and weight percent of the poly(acrylic acid)-b-poly(butyl methacrylate)-b-poly(acrylic acid) is about 20-40%, and the weight percent is calculated based on total weight of the layer.

In one example of the first embodiment, the first copolymer having a plurality of the amide groups and poly(N-isopropyl acrylamide)-b-poly(butyl methacrylate)-b-poly (N-isopropyl acrylamide) has a weight average molecular weight between 21,000 and 34,000 Da, respectively.

In one example of the first embodiment, the second copolymer having a plurality of the carboxylic acid groups and poly(acrylic acid)-b-poly(butyl methacrylate)-b-poly (acrylic acid) has an weight average molecular weight between 25,000 and 32,000 Da, respectively.

In one example of the first embodiment, the porous substrate has an average pore size between 8 and 15 micron.

In a second embodiment, the invention provides a method for preparing platelet rich plasma (PRP). Specifically, the method for preparing platelet rich plasma is able to prevent the platelets from activation and damage during the separation. As a result, good qualities of the platelet rich plasma are obtained by the invented method.

Representatively, the method comprises following steps.

Step 1: contacting a blood sample with the platelet filtration membrane as defined in the first embodiment at about 30~40° C. for 10 minutes at least for adsorbing platelets onto the platelet filtration membrane.

Step 2: removing non-adsorbing content of the blood sample from the platelet filtration membrane at about 30~40° C. by a filtering process and the filtering rate is about 10 ml/min Step 3: washing the platelet filtration membrane obtained at step (2) by a first liquid at about 30~40° C.

Step 4: cooling the platelet filtration membrane obtained at step (3) to 0~10° C. for releasing the platelets from the platelet filtration membrane.

Step 5: washing the platelets released at step (4) by a second liquid at about 0~10° C. to a receiver for obtaining the platelet rich plasma.

In one example of the second embodiment, the blood sample is a whole blood sample.

In one example of the second embodiment, the first liquid is NaCl aqueous solution.

In one example of the second embodiment, the second liquid is NaCl aqueous solution.

In one example of the second embodiment, the platelet rich plasma has a platelet concentration of $7{\sim}8\times10^5$ platelets/µl.

In one example of the second embodiment, the platelet rich plasma comprises 55-85 pg/µl of platelet-derived growth factor (PDGF) and 400-520 ng/µl of transforming growth factor (TGF).

In one example of the second embodiment, the method for preparing platelet rich plasma has 75-90% of platelet recovery, 2-5% of red blood cell residual percent and less than 0.0025% of white blood cell residual percent.

In one representative example of the second embodiment, the method for preparing platelet rich plasma is described as follows. Prepare a filter assembly multiple platelet filtration membranes. Place the filter, 50 ml of whole blood sample and NaCl aqueous solution in a 37° C. oven for 10 minutes. Place another NaCl aqueous solution in a 4° C. refrigerator for 10 minutes. Load the whole blood sample into the filter at about 37° C. and filter the whole blood sample with a filtering rate about 10 ml/min During the filtering period, platelets are captured by the multiple platelet filtration membranes, but both of red blood cells and white blood cells are filtered out from the filter. As a result, the platelets are separated from the whole blood sample and stored in the filter at about 37° C. Wash the filter at about 37° C. by NaCl aqueous solution to remove residual whole blood sample. After the washing step, cool the filter storing the platelets to about 4° C. for 10 minutes at least to allow the multiple platelet filtration membranes release the platelets. Wash out the released platelets by another NaCl aqueous solution at about 4° C. and collect them in a receiver. Therefore, the platelet rich plasma is obtained. The collected volume of the platelet rich plasma is about 8 ml.

In one example of the second embodiment, the method condition and performance are list in Table 1.

TABLE 1

| Condition/Performance | Results |
| --- | --- |
| Sample volume | 50 ml of whole blood sample |
| Collected volume | 10 ml of platelet rich plasma |
| Filtering rate | 10 ml/min |
| Operating time(Adsorption/Filtration/Collection) | 20-30 minutes |
| Platelets concentration in the platelet rich plasma | $7.55 \pm 0.13 \times 10^5$ platelets/µl |
| PDGF content in the platelet rich plasma | $71 \pm 13$ pg/µl |
| TGF content in the platelet rich plasma | $463 \pm 48$ ng/µl |
| Platelets recovery % | 82.5% ± 3.7% |
| Red blood cell residue % | 3.1% ± 1.2% |
| White blood cell residue % | 0.002% ± 0.0005% |

The method is to capture platelets from the blood sample onto the platelet filtration membrane and release the platelets from the platelet filtration membrane at different temperature, respectively, because the invented platelet filtration membrane comprises the thermal-responsive copolymer and the protein-conjugated copolymer. Preferably, the mixture or composition comprises the thermal-responsive copolymer and the protein-conjugated copolymer, and captures/binds platelets from the blood sample at about 30-40° C., but releases/desorbs the platelets at about 0-20° C.

In a third embodiment, the invention provides a method for separating platelets from a blood sample. The method comprises following steps.

Step 1: contacting a blood sample with the platelet filtration membrane as defined in the first embodiment at about 30~40° C. for 10 minutes at least for adsorbing platelets onto the platelet filtration membrane.

Step 2: removing non-adsorbing content of the blood sample from the platelet filtration membrane at about 30~40° C. by a filtering process and the filtering rate is Step 3: washing the platelet filtration membrane obtained at step (2) by a liquid at about 30~40° C.

Step 4: cooling the platelet filtration membrane obtained at step (3) to 0~10° C. for releasing the platelets from the platelet filtration membrane, so as to separating the platelets from the blood sample.

In one example of the third embodiment, the blood sample is a whole blood sample.

In one example of the third embodiment, the method has 75-90% of platelet recovery percent, 2-5% of red blood cell residual percent and less than 0.0025% of white blood cell residual percent.

In conclusion, the invented platelet filtration membrane comprises the thermal-responsive copolymer and the protein-conjugated copolymer, so is good to capture platelets from the blood sample and release the platelets from the platelet filtration membrane at different temperature, respectively. Preferably, the platelet filtration membrane captures platelets from the blood sample onto its surfaces at about 30-40° C. and releases the platelets from its surfaces at about 0-10° C.

Furthermore, the aforementioned methods for preparing platelet rich plasma and platelets separation are able to prevent the platelets from activation during the process. As a result, PDGF and TGF are reserved in the platelet rich plasma content and good qualities of the platelets rich plasma are obtained.

Example 1: The Layer Composition of the Platelet Filtration Membrane

The layer composition of the platelet filtration membrane comprises 70-75 wt. % of poly(N-isopropyl acrylamide)-b-poly(butyl methacrylate)-b-poly(N-isopropyl acrylamide) and 25-30 wt. % of poly(acrylic acid)-b-poly(butyl methacrylate)-b-poly(acrylic acid) is about 20-40%, and the weight percent is calculated based on total weight of the layer. The aforementioned layer composition is coated on a porous PP substrate to form the platelet filtration membrane.

Representative physical properties of the platelet filtration membrane are list in Table 2.

Accordingly, the platelet filtration membrane is a thermal-responsive membrane and able to capture platelets from the blood sample and release the platelets from the platelet filtration membrane at different temperature, respectively.

Figure 3:
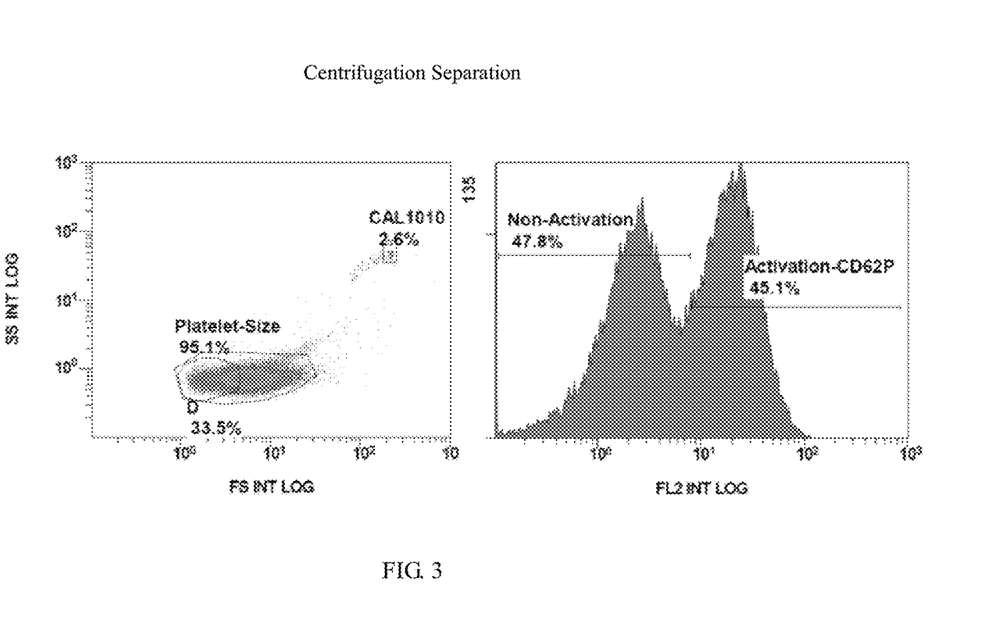
FIG. 3 is activation analytical plots of the platelets obtained by centrifugation separation.
Figure 4:
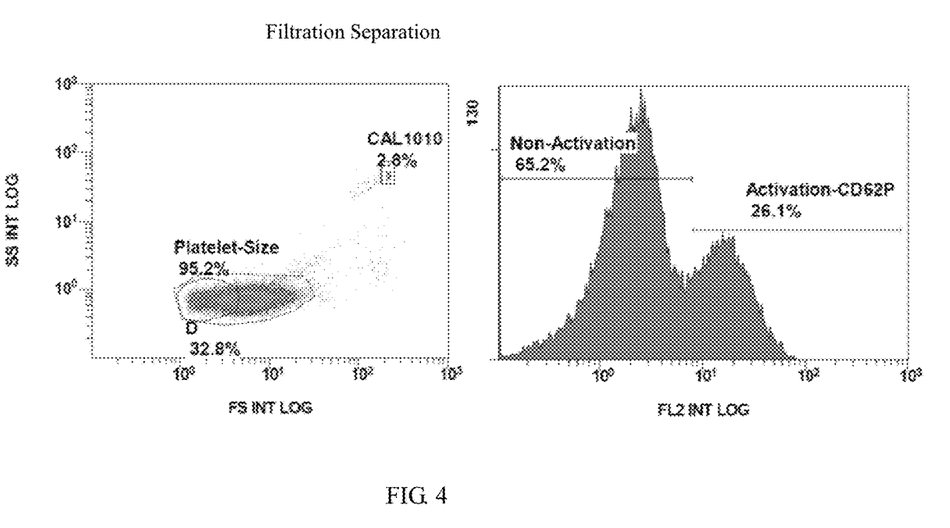
FIG. 4 is activation analytical plots of the platelets obtained by the platelet filtration membrane.

Performance Comparison of Platelet Centrifugation Method and the Platelets Filtration Method by the Platelet Filtration Membrane According to FIG. 3, the platelets obtained by the centrifugation method are more activated, and its activation CD62P is 45.1%, non-activation is 47.8%. On the contrast, the platelets obtained by the platelets filtration method are less activated. According to FIG. 4, the platelets obtained by the platelets filtration method have an activation CD62P only being 26.1% and non-activation is 65.2%. As a result, the platelet filtration membrane for preparing platelet rich plasma and platelets separation are able to prevent the platelets from activation during the process. Furthermore, PDGF and TGF are reserved in the platelet rich plasma content and good qualities of the platelets rich plasma are obtained.

Figure 5:
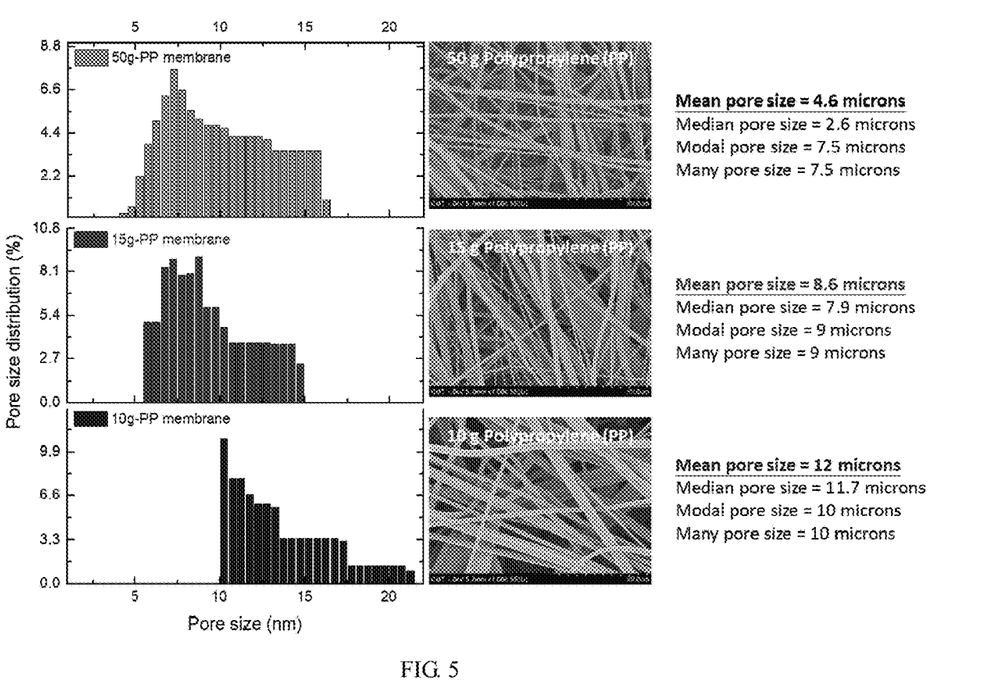
FIG. 5 illustrates pore size distribution of the platelet filtration membrane.

According to FIG. 5, the platelet filtration membranes prepared from porous PP substrates have 4.6 μm, 8.6 μm and 12 μm average pore size, respectively. The micron-size pore structure is to provide effective channels for filtering a blood sample.

Figure 6:
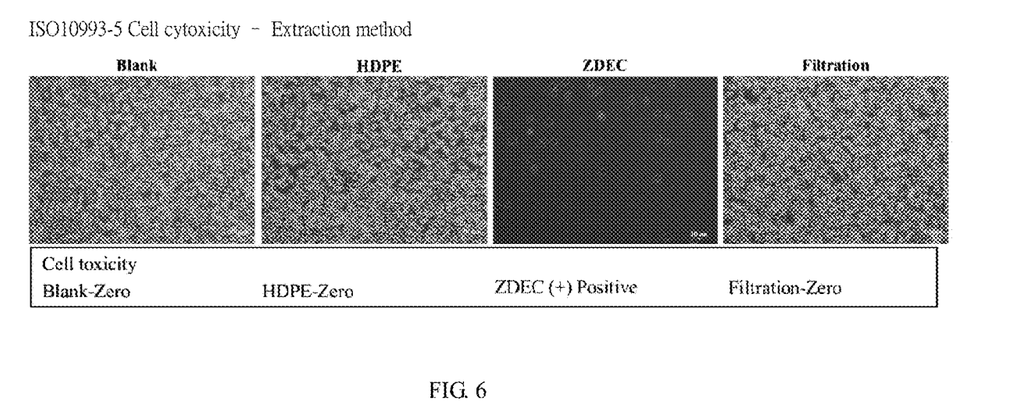
FIG. 6 shows cell toxicity measuring microscopy images of blank, HDPE, ZDEC and the platelet filtration membrane, respectively.

Cell toxicity of the platelet filtration membrane is measured according to ISO-10993-5 guidelines and the test cell is HT1080. HDPE is used as a positive control group which indicates no cell toxicity and ZDEC is used as a negative control group which indicates strong cell toxicity. The experimental result is shown in FIG. 6. Obviously, the microscopy images show the cell toxicity of the platelet filtration membrane is as the same as the positive control group. Therefore, the platelet filtration membrane has no cell toxicity and is biocompatible.

TABLE 2

| Physical properties | Thickness(nm) | | Water contact angle(degree) | | Porosity (%) | | Pore size(nm) | |
|---|---|---|---|---|---|---|---|---|
| | Temperature | | | | | | | |
| | 4° C. | 25° C. | 4° C. | 25° C. | 4° C. | 25° C. | 4° C. | 25° C. |
| Poly(propylene) Membrane | 1431 ± 25 | 1422 ± 39 | 105.1 ± 3.2 | 104.9 ± 4.6 | 62 ± 3 | 61 ± 4 | 12.2 ± 3.4 | 10.5 ± 4.9 |
| Copolymer-coated Membrane | 37.2 ± 2.1 | 20.2 ± 3.4 | 65.4 ± 5.7 | 82.4 ± 4.9 | 62 ± 3 | 62 ± 3 | 11.3 ± 2.9 | 10.9 ± 3.8 |

According to Table 2, both of thickness and water contact angle of the copolymer coated membrane (i.e., the platelet filtration membrane) are able to change at different temperature. Therefore, the platelet filtration membrane comprises a thermal-responsive layer and able to capture platelets from the blood sample and release the platelets from the layer at different temperature, respectively.

Figure 1:
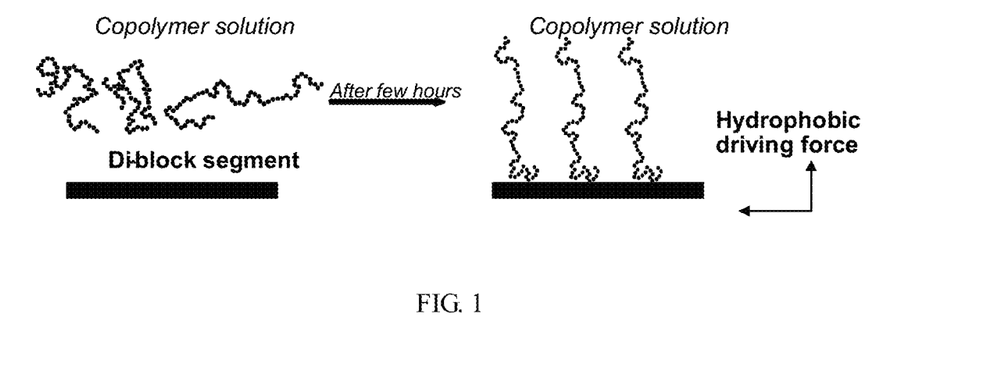
FIG. 1 illustrates the layer composition coat on the porous substrates.
Figure 2:
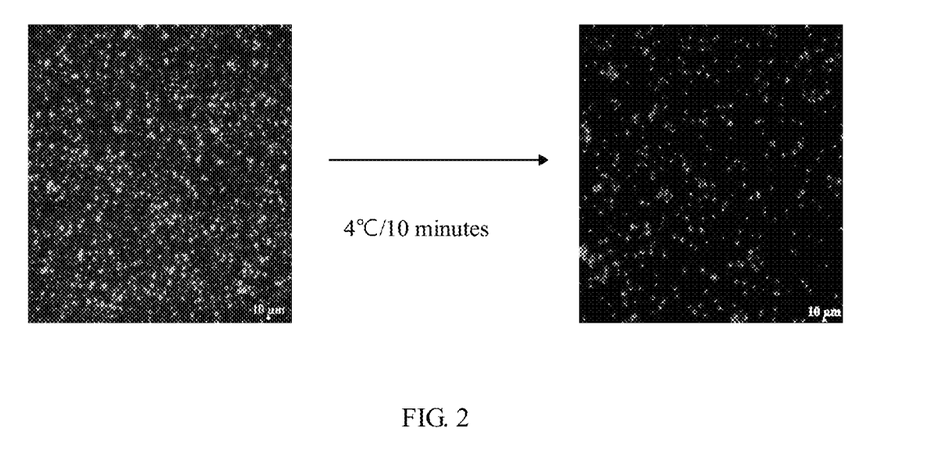
FIG. 2 shows a microscopy image of the platelet filtration membrane capturing the platelets (left side), and a microscopy image of the platelet filtration membrane releasing the platelets after storing at 4° C. for 10 minutes (right side)

According to FIG. 2, the photo at left side is an image of the platelet filtration membrane after capturing platelets, and there are many light spots on its surface. Place the platelet filtration membrane after capturing platelets at 4° C. for 10 minutes and observe its surface by microscopy. Obviously, the light spots on its surface decrease and that means the platelets release from the platelet filtration membrane.

Figure 7:
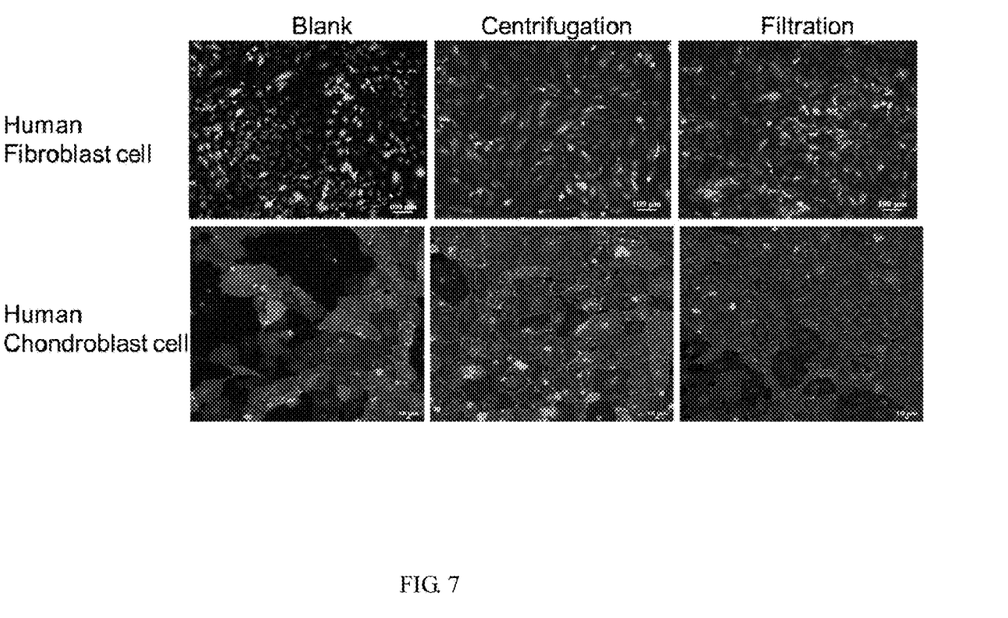
FIG. 7 shows microscopy images of human fibroblast cell and human Chondroblast cell obtained by centrifugation and filtration, respectively.

FIG. 7 is microscopy images which illustrate human fibroblast cell and human Chondroblast cell treated with centrifugation and filtration method.

Another coated layer composition of the platelet filtration membrane is (Poly(Styrene)$_{53}$-b-Poly(NIPAAm)$_{179}$), and control groups are (Poly(Styrene)$_{53}$-b-Poly(EGMA)$_{121}$) and Poly(Styrene)$_{53}$-b-Poly(AA)$_{175}$), respectively. According to Table 3, both of thickness and water contact angle of the (Poly(Styrene)$_{53}$-b-Poly(NIPAAm)$_{179}$) are able to change at different temperature. Therefore, the platelet filtration membrane comprises a thermal-responsive layer and able to capture platelets from the blood sample and release the platelets from the layer at different temperature, respectively.

TABLE 3

| | Thickness (nm) | | Contact angle (°) | |
|---|---|---|---|---|
| | 37° C. | 4° C. | 37° C. | 4° C. |
| Tissue culture plates | 0 | 0 | 67.28 ± 1.55 | 66.19 ± 2.03 |
| Poly(styrene)$_{53}$-b-Poly(NIPAAm)$_{179}$ | 20.19 ± 3.66 | 34.82 ± 4.31 | 83.13 ± 2.13 | 61.49 ± 3.29 |
| Poly(styrene)$_{53}$-b-Poly(EGMA)$_{121}$ | 16.89 ± 6.23 | 17.21 ± 5.57 | 51.41 ± 1.25 | 50.85 ± 2.41 |
| Poly(styrene)$_{53}$-b-Poly(AA)$_{175}$ | 25.98 ± 7.13 | 24.89 ± 4.76 | 35.71 ± 1.89 | 34.24 ± 2.11 |

Figure 8:
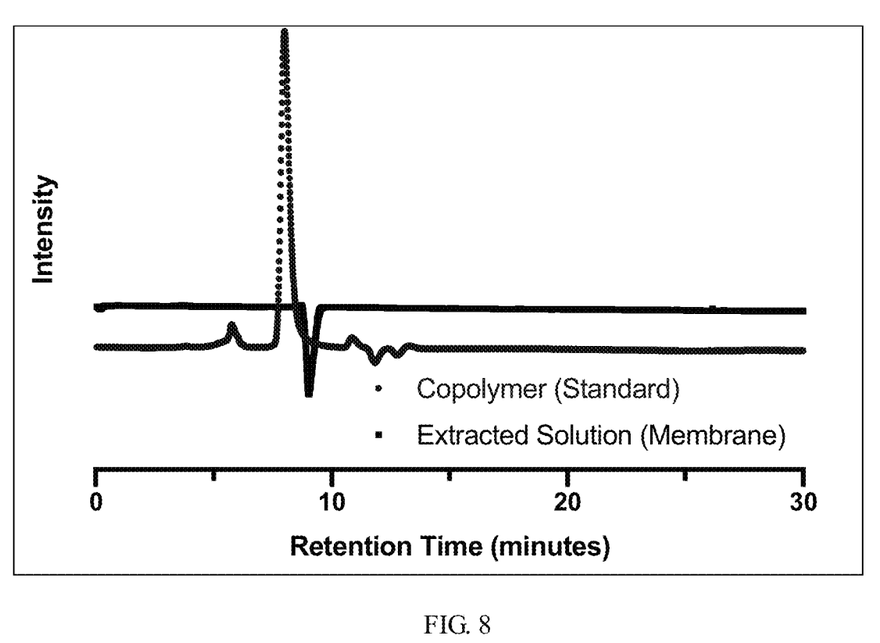
FIG. 8 is a overlapped chromatogram of the copolymer and the extract solution of the platelet filtration membrane.

The stability of the platelet filtration membrane is evaluated by analyzing stability of the coating layer. Generally, stable platelet filtration membranes do not lost the coated layer composition in an extraction process. As a result, we use HPLC to analyze extracted solution of the platelet filtration membrane. The analyzed HPLC result is shown in FIG. 8 and there is no peak of the coating copolymer found in the extracted solution of the platelet filtration membrane. Therefore, the platelet filtration membrane is stable and does not lose its performance.

Figure 9:
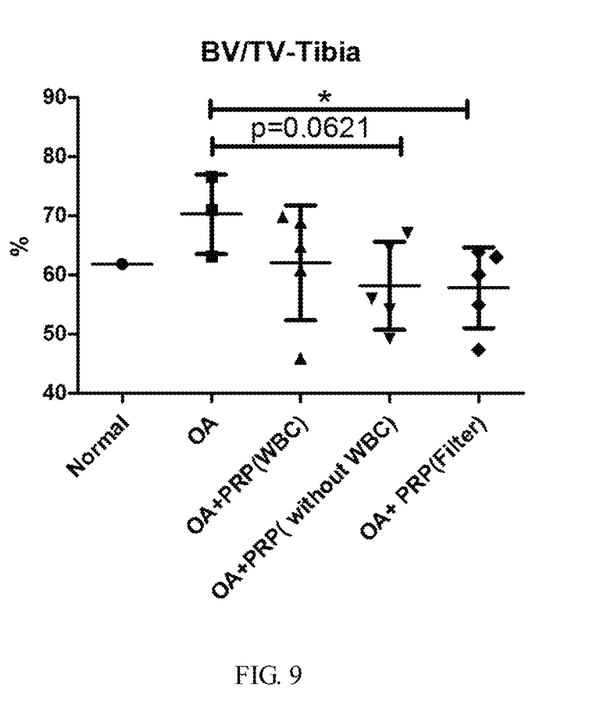
FIG. 9 is an effect analysis plot of the platelet rich plasma obtained by the invention in treating arthritis rats.

Furthermore, the platelet rich plasma obtained from the invention is evaluated its performance to treat arthritis. The test animal is rat. The experimental results are list in Table 4 and FIG. 9. According to Modified K-L grade analysis, the therapeutic effect of the platelet rich plasma obtained from the filtration method is much better than one obtained from centrifugation method.

TABLE 4

| Groups | 2 weeks | 4 weeks | 6 weeks |
|---|---|---|---|
| No therapy | 4.0 ± 0.0 | 3.8 ± 0.7 | 3.7 ± 0.5 |
| PRP(Filtration) | 3.2 ± 0.6 | 2.8 ± 0.6 | 2.6 ± 0.4 |
| PRP without WBC(centrifugation) | 3.3 ± 0.3 | 3.0 ± 0.2 | 3.3 ± 0.6 |
| PRP with WBC (centrifugation) | 3.5 ± 0.4 | 3.2 ± 0.3 | 3.3 ± 0.7 |

Accordingly, the platelet filtration membrane comprises a layer that coated on surfaces of a porous substrate. The porous substrate has a micron-size pore structure for providing effective channels for filtering a blood sample. Moreover, the layer has a nanometer thickness and comprises at least two types of copolymer. One is a thermal responsive type copolymer and another one is a protein-conjugated type copolymer, so as to capture platelets from the blood sample onto it and release the platelets from the layer at different temperature, respectively. Preferably, the layer captures platelets from the blood sample onto it at about 30-40° C. and releases the platelets from the layer at about 0-20° C. Furthermore, the aforementioned methods for preparing platelet rich plasma and platelets separation by using the platelet filtration membrane are able to prevent the platelets from activation during the process. As a result, PDGF and TGF are reserved in the platelet rich plasma content and good qualities of the platelets rich plasma are obtained. Typically, the aforementioned methods for preparing platelet rich plasma and platelets separation by using the platelet filtration membrane have 75-90% of platelet recovery percent, 2-5% of red blood cell residual percent and less than 0.0025% of white blood cell residual percent.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A platelet filtration membrane, comprising a layer that is coated on surfaces of a porous substrate, wherein the layer comprises at least a first copolymer comprising a plurality of amide groups and a second copolymer comprising a plurality of carboxylic acid groups, and wherein the porous substrate comprises poly(ethylene), poly(propylene), poly(styrene), polyethylene terephthalate, polytetrafluoroethylene, polyvinylidene fluoride, ceramic or rayon.

2. The platelet filtration membrane of claim 1, wherein the layer has a thickness between 20 and 50 nm.

3. The platelet filtration membrane of claim 1, wherein the layer has a first water contact angle between 50 and 60 degree at about 37° C., and a second water contact angle between 20 and 40 degree at about 20° C.

4. The platelet filtration membrane of claim 1, wherein the first copolymer comprising a plurality of the amide groups comprises poly(N-isopropyl acrylamide)-poly(butyl methacrylate) or poly(N-isopropyl acrylamide)-poly(styrene).

5. The platelet filtration membrane of claim 1, wherein the second copolymer comprising a plurality of the carboxylic acid groups comprises poly(acrylic acid)-poly(butyl methacrylate).

6. The platelet filtration membrane of claim 1, wherein weight percent of the first copolymer comprising a plurality of the amide groups is about 60-80% and weight percent of the second copolymer comprising a plurality of the carboxylic acid groups is about 20-40%, and the weight percent is calculated based on total weight of the layer.

7. The platelet filtration membrane of claim 1, wherein the first copolymer comprising a plurality of the amide groups has a average molecular weight between 21,000 and 34,000 Da.

8. The platelet filtration membrane of claim 1, wherein the second copolymer comprising a plurality of the carboxylic acid groups has a average molecular weight between 25,000 and 32,000 Da.

9. The platelet filtration membrane of claim 1, wherein the porous substrate has an average pore size between 8 and 15 micron.

10. A method for preparing platelet rich plasma, comprising:
    (1) contacting a blood sample with the platelet filtration membrane as defined in claim 9 for at least 10 minutes at about 30-40° C. for adsorbing platelets onto the platelet filtration membrane;
    (2) removing non-adsorbing content of the blood sample from the platelet filtration membrane at about 30~40° C. by a filtering process and the filtering rate is about 10 ml/min;
    (3) washing the platelet filtration membrane obtained at step (2) by a first liquid at about 30~40° C.;

(4) cooling the platelet filtration membrane obtained at step (3) to 0~10° C. for releasing the platelets from the platelet filtration membrane; and (5) washing the platelets released at step (4) by a second liquid at about 0~10° C. to a receiver for obtaining the platelet rich plasma.

11. The method for preparing platelet rich plasma of claim 10, wherein the blood sample is a whole blood sample.

12. The method for preparing platelet rich plasma of claim 10, wherein the first liquid is NaCl aqueous solution.

13. The method for preparing platelet rich plasma of claim 10, wherein the second liquid is NaCl aqueous solution.

14. The method for preparing platelet rich plasma of claim 10, wherein the platelet rich plasma has a platelet concentration of $7~8\times10^5$ platelets/μl.

15. The method for preparing platelet rich plasma of claim 10, wherein the platelet rich plasma comprises 55-85 pg/μl of platelet-derived growth factor and 400-520 ng/μl of transforming growth factor.

16. The method for preparing platelet rich plasma of claim 10, having 75-90% of platelet recovery percent, 2-5% of red blood cell residual percent and less than 0.0025% of white blood cell residual percent.

17. A method for separating platelets from a blood sample, comprising:
(1) contacting a blood sample with the platelet filtration membrane as defined in claim 9 for at least 10 minutes at about 30-40° C. for adsorbing platelets onto the platelet filtration membrane;
(2) removing non-adsorbing content of the blood sample from the platelet filtration membrane at about 30~40° C. by a filtering process and the filtering is about 10 ml/min;
(3) washing the platelet filtration membrane obtained at step (2) by a liquid at about 30~40° C.; and
(4) cooling the platelet filtration membrane obtained at step (3) to 0~10° C. for releasing the platelets from the platelet filtration membrane, so as to separate the platelets from the blood sample.

18. The method for separating platelets from a blood sample of claim 17, wherein the blood sample is a whole blood sample.

19. The method for separating platelets from a blood sample of claim 17, having 75-90% of platelet recovery, 2-5% of red blood cell residual percent and less than 0.0025% of white blood cell residual percent.

* * * * *